United States Patent [19]
Acosta-Cuello et al.

[11] Patent Number: 5,807,578
[45] Date of Patent: Sep. 15, 1998

[54] FAST-MELT TABLET AND METHOD OF MAKING SAME

[75] Inventors: Tabaré R. Acosta-Cuello, Montreal; Aomar Ouali, Boisbriand, both of Canada

[73] Assignee: LAB Pharmaceutical Research International Inc., Quebec, Canada

[21] Appl. No.: 752,026

[22] Filed: Nov. 19, 1996

(Under 37 CFR 1.47)

Related U.S. Application Data

[63] Continuation-in-part of Ser. No. 562,057, Nov. 22, 1995.

[51] Int. Cl.⁶ ................................................. A61K 9/46
[52] U.S. Cl. ........................ 424/466; 424/441; 424/465; 424/474; 514/819
[58] Field of Search ................................. 424/466, 441, 424/489, 465, 474

[56] References Cited

U.S. PATENT DOCUMENTS

| | | | |
|---|---|---|---|
| 3,493,652 | 2/1970 | Hartman | 424/94 |
| 3,622,677 | 11/1971 | Short et al. | 424/361 |
| 3,639,168 | 2/1972 | Monti et al. | 127/29 |
| 3,843,778 | 10/1974 | Diamond et al. | 424/38 |
| 4,017,598 | 4/1977 | Ohno et al. | 424/35 |
| 4,079,125 | 3/1978 | Sipos | 424/32 |
| 4,115,553 | 9/1978 | Rubino et al. | 424/155 |
| 4,163,777 | 8/1979 | Mitra | 424/21 |
| 4,230,693 | 10/1980 | Izzo et al. | 424/156 |
| 4,271,142 | 6/1981 | Puglia et al. | 424/14 |
| 4,327,076 | 4/1982 | Puglia et al. | 424/38 |
| 4,327,077 | 4/1982 | Puglia et al. | 424/38 |
| 4,369,308 | 1/1983 | Trubiano | 536/106 |
| 4,425,332 | 1/1984 | James | 424/94 |
| 4,517,179 | 5/1985 | Raghunathan | 514/249 |
| 4,581,381 | 4/1986 | Morris et al. | 514/819 |
| 4,605,551 | 8/1986 | Buehler et al. | 424/38 |
| 4,609,543 | 9/1986 | Morris et al. | 424/38 |
| 4,613,497 | 9/1986 | Chavkin | 424/44 |
| 4,996,058 | 2/1991 | Sinnreich | 424/462 |
| 5,069,910 | 12/1991 | Kovacic et al. | 424/464 |
| 5,178,878 | 1/1993 | Wehling et al. | 424/466 |
| 5,223,264 | 6/1993 | Wehling et al. | 424/466 |
| 5,254,355 | 10/1993 | Smith et al. | 426/285 |
| 5,302,396 | 4/1994 | Phadke et al. | 424/465 |
| 5,320,848 | 6/1994 | Geyer et al. | 424/441 |
| 5,320,852 | 6/1994 | Moest | 424/464 |
| 5,348,745 | 9/1994 | Daher | 424/466 |
| 5,496,563 | 3/1996 | Ito et al. | 424/489 |
| 5,556,640 | 9/1996 | Ito et al. | 424/489 |

FOREIGN PATENT DOCUMENTS

| | | |
|---|---|---|
| 1258428 | 8/1989 | Canada . |
| 0 662 320 | 7/1995 | European Pat. Off. . |
| WO 91/04757 | 4/1991 | WIPO . |
| WO 93/01805 | 2/1993 | WIPO . |

*Primary Examiner*—Thurman K. Page
*Assistant Examiner*—James M. Spear
*Attorney, Agent, or Firm*—Cushman, Darby, Cushman IP Group of Pillsbury, Madison & Sutro LLP

[57] ABSTRACT

Provided is an improved, fast-melting solid dosage form which readily disintegrates when placed in the mouth. The solid dosage form preferably being a tablet comprising the following primary ingredients whose proportions are calculated as weight percent on the total weight of the tablet: (a) from about 30 to 50 weight percent, of a pharmaceutically acceptable active ingredient component; (b) an effervescent couple consisting of about 2 to 5 weight percent of an effervescence base about 2 to 5 weight percent of an effervescence acid suitable for achieving a gas evolving reaction with the effervescence base upon being contacted with an aqueous solution such as saliva; (c) about 35 to 50 weight percent of a pharmaceutically acceptable starch as a bulking and disintegrating agent; (d) about 0.04 to 1 weight percent of a starch degrading enzyme; and (e) about 2 to 5 weight percent of a tablet lubricant. Additionally, the tablet may comprise flavoring agents. The tablet is formed of granules of a mixture of the active ingredient component, the effervescence base, and the starch, admixed to a powderous blend of the remaining ingredients, subsequently compressed in tablet form. Also provided is a method of making the solid dosage form of the present invention.

21 Claims, No Drawings

FAST-MELT TABLET AND METHOD OF MAKING SAME

REFERENCE TO OTHER APPLICATIONS

This application is a continuation-in-part of application Ser. No. 08/562,057, filed Nov. 22, 1995.

BACKGROUND OF THE INVENTION

1. Field Of The Invention

The invention relates to the field of solid dosage forms for ingestion of active substances which are absorbed in the mouth or digestive tract. More specifically, the invention is concerned with solid, effervescent and "fast-melting" tablets. Most particularly, the invention is concerned with tablet formulations comprising one or more active substances, an effervescent couple such as sodium bicarbonate and malic acid, a swelling and disintegrating agent and an enzyme acting as a disintegration regulating agent hereinafter termed disintegration modulator. In one embodiment, the active substances may be antacids such as calcium carbonate and magnesium hydroxide.

2. Description Of The Prior Art

The use of compressed tablet compositions is well known for oral administration of various active substances such as antacids. The use of antacids such as calcium carbonate and magnesium hydroxide to treat gastric hyperacidity is also well known.

Also known is the use of sodium bicarbonate and malic acid as an effervescent couple which, when contacted with saliva or other aqueous solutions, undergoes an effervescent reaction.

The use of bulking and disintegrating agents such as sugars, polyhydric alcohols, e.g. mannitol, sorbitol and xylitol and starches is also known.

Solid dosage forms destined for ingestion, including antacid formulations, have been prepared and marketed in various forms such as tablets, lozenges and powders. Many solid formulations do not readily disintegrate in the mouth and impart a chalky taste.

Canadian Patent No. 1,258,428, Damini et al., provides a soft candy antacid composition comprising about 5–50 weight percent of antacid ingredient, about 50–95 weight percent of a confectionary base (fondant) and a plasticizer to avoid crystallization of the sugars contained in the confectionary base. When placed in the mouth, the soft candy will gradually liquefy to release the antacid ingredients while masking their taste.

U.S. Pat No. 5,178,878 and 5,223,264, to Wehling et al. disclose compressed tablet compositions comprising an effervescent couple disintegration agent, an effective amount of active ingredient such as an antacid, and a non-effervescent disintegrant such as starch in a proportion up to 20 weight percent and preferably 2 to 10 weight percent of composition (U.S. Pat. No. 5,223,264, column 6, lines 62–64, and U.S. Pat. No. 5,178,878, column 7, lines 48–51,). When orally ingested, the tablets are said to dissolve in the mouth in less than 10 minutes and desirably between 7 minutes and 30 seconds.

U.S. Pat. No. 4,369,308, Trubiano, discloses the use of various low-swelling starches as tablet disintegrants. The starches are said to be useful in many tableting methods in amounts of about 10 weight percent or less.

It is apparent that starches, when used as tablet swelling and disintegrating agents are typically present in a proportion of only about 20 weight percent or less and nothing is added to the starches to cause a rapid degradation of the starches thereby assisting the faster "melting" of the tablet.

Thus, there remains a need for an improved solid dosage form which not only stores well and does not easily chip or break during handling but also very quickly dissolves in the mouth, i.e. in less than 30 seconds, preferably less than about 20 seconds, and which imparts a pleasant mouth feel, a palatable taste and freshens breath.

SUMMARY OF THE INVENTION

This invention is the result of a project whose goal was the development of an improved solid dosage form which upon ingestion would immediately "melt" in the mouth and disintegrate in a few seconds. Corollary objectives were to provide solid formulations which would store well, would not collapse or fragment during shipping and handling of the product, and yet when placed in the mouth would immediately disintegrate with a good mouth feel with no apparent aftertaste and at the same time freshen breath.

It was surprisingly discovered that those goals and objectives could be achieved by using a starch as a bulking and disintegrating agent and, at the same time, an effervescent couple as a supplemental disintegrating agent and a starch degrading enzyme as a disintegration modulator. Thus, an important synergistic effect of very rapid tablet dissolution in aqueous environments is observed when using a starch together with an effervescent couple and a starch degrading enzyme. In a preferred embodiment, a large proportion of starch is used, i.e. in the order of 35 to 50 percent by weight.

Accordingly, the invention provides, in one aspect, a fast-melting solid dosage form, preferably an antacid tablet, which will readily disintegrate when placed in the mouth, said solid dosage form comprising the following primary ingredients:

(a) a therapeutically effective amount of a pharmaceutically acceptable active ingredient component;

(b) an effervescent couple consisting of an effervescence base and an effervescence acid suitable for achieving a gas evolving reaction with said effervescence based upon said effervescent couple being contacted with an aqueous solution;

(c) a bulking and disintegrating agent consisting of starch;

(d) at least one starch degrading enzyme suitable for achieving a starch degradation reaction upon said solid dosage form being contacted with an aqueous solution;

(e) a solid dosage form lubricant.

In a preferred embodiment, the primary ingredients will be present in the following proportions expressed as weight percentages:

(a) about 25 to 50 weight percent, of the pharmaceutically acceptable active ingredient;

(b) about 3 to 5 weight percent of the effervescence base and about 3 to 5 weight percent of the effervescence acid;

(c) about 35 to 50 weight percent of the pharmaceutically acceptable starch;

(d) about 0.04 to 2 weight percent of the starch-degrading enzyme;

(e) about 2 to 5 weight percent of the lubricant.

In a further aspect, the invention provides a method of making the solid formulations of the present invention. The method can be summarized as comprising the steps of:

(a) sieving to powder and mixing the primary internal phase ingredients, comprising the active ingredient component, the starch and the effervescence base to obtain an internal phase mixture;

(b) wet granulating said mixture to obtain small granules;

(c) sieving said granules to a generally uniform size distribution of said granules;

(d) mixing said granules with the external phase primary ingredients comprising the effervescence acid, the starch degrading enzyme and the solid dosage form lubricant;

(e) compressing the resulting mixture in a compression device, preferably a tablet press, to obtain a porous and fast-melting tablet.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

DETAILED DESCRIPTION OF THE PREFERRED EMBODIMENTS

A solid dosage form according to a preferred embodiment of the present invention is a compressed tablet suitable for ingestion. The expression "pharmaceutical active ingredient" as used in this disclosure means a drug, vitamin or mineral. Drugs may include, without limitation, antacids, antibiotics, antiseptics, antiulcerative agents, analgesics, antihistamines, antivirals, antiparasitic drugs, laxatives, gastro-intestinal motility modifying agents, antinauseants, antihyperlipidaemic agents, anti-inflammatories, antidiuretics, antiflatulents, tranquillizers, stimulants, sedatives, antihypertensives, anticonvulsants, antiepileptics, oncologic therapy, decongestants, antiasthmatics, betablockers and combinations thereof. In a most preferred embodiment, the pharmaceutical active ingredient comprised in the solid dosage form is an antacid or a mixture of antacids. However, the present invention is not intended to be strictly limited to antacids as active ingredients.

Hence, in a most preferred and illustrative embodiment, the pharmaceutical active ingredient is an antacid or a mixture of antacids. Examples of antacids are calcium carbonate, magnesium carbonate, magnesium hydroxide, magnesium oxide, aluminum hydroxide, bismuth subsalicyclate, aluminum-magnesium hydroxide, and combinations thereof.

Preferably, the solid antacid formulation will comprise about 25 to 50 weight percent of antacid powder, based on the weight of the solid antacid formulation. Most preferably, the formulation will comprise about 20 to 30 weight percent of calcium carbonate and about 5 to 20 weight percent of magnesium hydroxide.

The effervescent couple will comprise two dry ingredients which, when contacted with aqueous solutions, will undergo an effervescent reaction. Effervescence relates to the generation and release of gas bubbles during the effervescent reaction. In an effervescent couple, there is usually an effervescence base and an effervescence acid. Representative of an effervescence base are: sodium carbonate, sodium bicarbonate, potassium carbonate, potassium bicarbonate, and calcium carbonate. Representative of an effervescence acid are: malic acid, maleic acid, tartaric acid, citric acid and alginic acid. Preferably, the effervescence base will be sodium bicarbonate and the effervescence acid will be malic acid.

Preferably, the solid antacid formulation will comprise about 3 to 5 weight percent, of the effervescence base, and about 3 to 5 weight percent of the effervescence acid.

However, it is noted that a portion of the antacid active ingredient, for example calcium carbonate, may also contribute to the effervescence base.

The bulking and disintegrating agent will consist of starches, preferably corn starch, or modified starches, preferably sodium starch glycolate (Explotab®) or mixtures thereof, in any proportions. Thus, throughout this patent application, the word starch is used in a general sense as encompassing various starches and modified starches. Preferably the starch will be present in a proportion of about at least 40 weight percent, and most preferably, at least 45 weight percent. The starch will of course be pharmaceutically acceptable and should contribute to the palatability of the formulation. Another advantage conferred by the high proportion of starch in the antacid tablet formulation is the increased salivation effect when the tablet is placed in the mouth. This increased salivation is induced by the porous nature of the starch. Increased salivation favors rapid ingestion of the active ingredients and rapid disintegration of the tablet. The porosity of the starch base allows a rapid penetration of saliva thereby assisting in the "fast-melting" of the tablet.

Furthermore, the starch degrading enzymes will have a synergistic effect on the "fast-melting" of the tablet. Indeed, the enzymes upon being contacted with an aqueous solution will immediately begin to convert the starch to mono and polysaccharides which quickly dissolve in the aqueous environment and further contribute to improving the taste of the tablet and increasing salivation. Mouth dryness is also reduced because of the soluble nature of the enzyme degradation products, which allows for a faster removal from the ingestion site by dissolution.

It is of course to be understood that enzymes will be chosen for their degradation effect on the starch and also for their stability over time, i.e. during the shelf-life of the tablet. Advantageously, the enzyme will be chosen from the group of starch degrading enzymes comprising α-amylase, β-amylase, amyloglucosidase, debranching enzymes and glucose-fructose isomerase. Most preferably, the enzymes will be an equal mixture of amyloglucosidase and a-amylase. For example, a mixture of equal weights of Novo Nordisk Biochem North America Inc.'s Fungamyl/2500 BG™(α-amylase from Aspergillus oryzae, 1830/AF 13146, ID#110530 (Enzyme 1) and amyloglucosidase (AMG), Sample/AM20037, ID#110530 (Enzyme 2), were found to be adequate.

In accordance with the present invention, the "fast-melting" will readily occur within a matter of seconds, typically within about 20 seconds.

The solid effervescent formulation may have incorporated therein optional ingredients in order to confer it more desirable properties. Representative optional ingredients include: flavoring, aroma and breath freshening agents such as peppermint oil and peppermint aroma, and natural or artificial sweeteners such as aspartame. The selection of such optional ingredients and their proportions is well within those skilled in the art.

The solid effervescent formulation is preferably intended to be manufactured in compressed tablet form. Accordingly, when formulated as a tablet, the formulation will preferably consist of an admixture and direct compression of a mixture of an internal phase consisting of granules and a powderous external phase. In a most preferred embodiment, the internal phase will comprise granules each containing a mixture of the antacid active ingredient, the corn starch bulking and disintegrating agent, the effervescence base and the aroma agent. In accordance with this invention, the internal phase will be prepared by mixing and sieving the dry ingredients and wet granulating them with purified water USP and sizing them with a sieve. The granules can then be admixed with a powderous blend of the external phase ingredients.

In a most preferred embodiment, the external phase will contain the effervescence acid, one or more starch degrading enzymes, a tabletting lubricant, a sweetener and an aroma agent.

The admixture of internal and external phase ingredients can be directly compressed in tablet form using conventional hydraulic punch equipment. The resulting tablet exhibits a smooth surface, stores well and is sufficiently chip resistant to be easily packaged, shipped and handled.

Advantageously, the tablet will also be provided with a protective and flavoring coating consisting of polyols and flavoring agents, easily known by those skilled in the art. For example, a tablet made in accordance with the present invention could be spray coated on top and bottom when passing on a sieve conveyor. For example, the polyols coating could comprise a mixture of mannitol, purified water, propylene glycol and xylitol and optional further flavoring agents. Colorants and other texture modifiers could also be added. The coated tablets exhibit further mechanical resistance for greater stability and improved shelf-life.

Examples Of The Invention

The following example represents a most preferred embodiment of the present invention and is provided merely for illustrative purposes.

Example 1

Antacid tablets were prepared in accordance with the present invention. The tablets were formed by hydraulic punching of a mixture of spherical granules (internal phase) and a blend of powdered ingredients (external phase). The formulation of the internal and external phases was as follows:

In a Patterson Kelly, 8 pint, V-blender, the internal phase ingredients were intimately mixed. This mixture was then wetted with purified water USP, dried and granulated in a fluidized-bed, Glatt CPGC-3 granulator. The resulting granules were then sieved to a substantially uniform size range of spherical granules. The granules were then admixed to a blend of the powdered external phase ingredients. The resulting mixture was then formed into tablets using a compression device such as a conventional hydraulic punch.

The tablets were sufficiently hard to resist chipping and breakage during normal handling. However, when placed in the mouth, the tablets rapidly collapsed and disintegrated with concomitant effervescence, i.e. in about 20 seconds, and left a pleasant minty, taste and freshness of breath.

The disintegration of the tablet was shown to increase salivation and favor rapid ingestion of the active antacid ingredients.

Although the invention has been described above with respect to one specific form, it will be evident to a person skilled in the art that it may be modified and refined in various ways. It is therefore wished to have it understood that the present invention should not be limited in scope, except by the terms of the following claims.

What is claimed is:

1. A fast-melting solid dosage form destined for ingestion and which will readily disintegrate when placed in the mouth, said solid dosage form comprising the following primary ingredients:
   (a) a therapeutically effective amount of a pharmaceutically acceptable active ingredient component;
   (b) an effervescent couple consisting of an effervescence base and an effervescence acid suitable for achieving a gas evolving reaction with said effervescence based upon said effervescent couple being contacted with an aqueous solution;
   (c) a bulking and disintegrating agent consisting of starch;

INTERNAL PHASE

| ingredient | nature | weight % based on total tablet weight | weight % based on total weight of internal phase ingredients only |
|---|---|---|---|
| calcium carbonate | active ingredient and effervescence base | 34.41 | 40.72 |
| magnesium hydroxide | active ingredient | 8.14 | 6.88 |
| corn starch | swelling, disintegrating and salivation agent | 47.43 | 40.08 |
| sodium carbonate | effervescence base | 3.71 | 3.13 |
| peppermint oil W381025F | aroma | | |

EXTERNAL PHASE

| ingredient | nature | weight % based on total tablet weight | weight % based on total weight of external phase ingredients only |
|---|---|---|---|
| talc | lubricant | 14.71 | 2.35 |
| malic acid | effervescence acid | 24.82 | 3.97 |
| enzyme, equal parts of α-amytase and amyloglucosidase | starch degradation agent | 0.29 | 0.05 |
| peppermint aroma WL15,666 | aroma | | |
| aspartame | artificial sweetener | 8.44 | 1.35 |

(d) at least one starch degrading enzyme suitable for achieving a starch degradation reaction upon said solid dosage form being contacted with an aqueous solution;

(e) a solid dosage form lubricant.

2. A solid dosage form according to claim 1 wherein said starch is present in a proportion of 40 to 50 weight percent based on the total weight of said solid dosage form.

3. A solid dosage form according to claim 1 wherein said starch degrading enzyme is selected from the group of enzymes consisting of α-amylase, β-amylase, amyloglucosidase, and glucose-fructose isomerase.

4. A solid dosage form according to claim 2 wherein said starch degrading enzyme is selected from the group of enzymes consisting of α-amylase, β-amylase, amyloglucosidase, and glucose-fructose isomerase.

5. A solid dosage form according to claim 3 wherein said starch degrading enzyme is a mixture of amyloglucosidase and α-amylase.

6. A fast-melting antacid tablet which will readily disintegrate when placed in the mouth, said antacid tablet comprising the following ingredients whose proportions are calculated as weight percent on the total weight of the tablet:

(a) an antacid component comprising about 33 weight percent of calcium carbonate and about 6.5 weight percent of magnesium hydroxide;

(b) an effervescent couple consisting of about 3.5 weight percent of sodium bicarbonate as an effervescence base and about 4 weight percent of malic acid as an effervescence acid suitable for achieving a gas evolving reaction with said effervescence based upon said effervescent couple being contacted with an aqueous solution;

(c) a bulking and disintegrating agent consisting of corn starch in a proportion of about 40 weight percent;

(d) a starch-degrading enzyme in a proportion of about 0.05 weight percent; and (e) a tablet lubricant consisting of talc in a proportion of about 2.4 weight percent.

7. A solid dosage form according to claim 3 wherein the primary ingredients are present in the following proportions calculated as weight percentages of the total weight of the solid dosage form:

(a) about 25 to 50 weight percent, of a pharmaceutically acceptable active ingredient;

(b) about 3 to 5 weight percent of an effervescence base and about 3 to 5 weight percent of the effervescence acid;

(c) about 35 to 50 weight percent of the pharmaceutically acceptable starch;

(d) about 0.04 to 2 weight percent of the starch-degrading enzyme;

(e) about 2 to 5 weight percent of the lubricant.

8. A solid dosage form according to claim 7 wherein said solid dosage form is an antacid.

9. A solid dosage form according to claim 8 wherein said solid dosage form is an antacid tablet.

10. A solid dosage form according to claim 9 wherein said solid dosage form has an exterior coating comprising polyols so as to protect and impart a pleasant taste to said solid dosage form.

11. An antacid tablet according to claim 9 wherein the starch is corn starch.

12. An antacid tablet according to claim 11 wherein said tablet comprising an internal phase consisting of granules of a mixture of internal phase ingredients comprising as primary ingredients the antacid component, the corn starch and the effervescence base, said internal phase ingredients being in admixture and in direct compression with an external phase comprising as primary ingredients the effervescence acid, the enzyme and the tablet lubricant.

13. The antacid tablet according to claim 12 wherein said antacid active component consists of a mixture of about 30 to 35 weight percent of calcium carbonate and about 6 to 7 weight percent of magnesium hydroxide.

14. The antacid tablet according to claim 13 wherein said effervescence couple consists of sodium bicarbonate as the effervescence base and malic acid as the effervescence acid.

15. The antacid tablet according to claim 14 which additionally includes an effective amount of a sweetening agent.

16. The antacid tablet according to claim 15 which additionally includes an effective amount of at least one breath freshening agent.

17. A method for treating gastric hyperacidity in humans comprising orally administering a therapeutically effective dosage of the tablet of claim 6.

18. A method for forming a tablet as defined in claim 1, said method comprising the steps of:

(a) sieving to powder and mixing the primary internal phase ingredients, comprising the active ingredient component, the starch and the effervescence base to obtain an internal phase mixture;

(b) wet granulating said mixture to obtain small granules;

(c) sieving said granules to a generally uniform size distribution of said granules;

(d) mixing said granules with the external phase primary ingredients comprising the effervescence acid, and the tablet lubricant;

(e) compressing the resulting mixture in a compression device to obtain a porous and fast-melting antacid tablet.

19. The method of claim 18 wherein said external phase ingredients additionally comprise at least one flavoring agent.

20. The method of claim 18 wherein said antacid component consists of a mixture of about 30 to 35 weight percent of calcium carbonate and about 6 to 7 weight percent of magnesium hydroxide, said weight percentages being calculated on the total weight of the resulting tablet.

21. A method for treating gastric hyperacidity in humans comprising orally administering a therapeutically effective dosage of the solid dosage form of claim 6.

* * * * *